United States Patent [19]

DiSanto

[11] Patent Number: 6,117,912
[45] Date of Patent: Sep. 12, 2000

[54] SUBLINGUAL AND BUCCAL ADMINISTRATION OF SELEGILINE FOR TREATING CERTAIN SELEGILINE-RESPONSIVE DISEASES AND CONDITIONS

[75] Inventor: Anthony R. DiSanto, Gobles, Mich.

[73] Assignee: Somerset Pharmaceuticals, Inc., Tampa, Fla.

[21] Appl. No.: 09/066,916

[22] Filed: Apr. 28, 1998

Related U.S. Application Data

[63] Continuation of application No. PCT/US96/17745, Nov. 5, 1996.
[60] Provisional application No. 60/007,325, Nov. 6, 1995.

[51] Int. Cl.[7] .................................................. A01N 33/02
[52] U.S. Cl. ............................................................ 514/654
[58] Field of Search ............................................. 514/654

[56] References Cited

U.S. PATENT DOCUMENTS

| | | |
|---|---|---|
| 4,812,481 | 3/1989 | Reischig et al. . |
| 4,826,875 | 5/1989 | Chiesi . |
| 4,861,800 | 8/1989 | Buyske . |
| 5,057,321 | 10/1991 | Edgren et al. . |
| 5,151,419 | 9/1992 | Perenyi et al. . |
| 5,151,449 | 9/1992 | Milgram . |
| 5,192,550 | 3/1993 | Edgren et al. . |
| 5,192,808 | 3/1993 | Ruehl et al. . |
| 5,221,536 | 6/1993 | Edgren et al. . |
| 5,242,950 | 9/1993 | Fries Hastings . |
| 5,266,332 | 11/1993 | Dong et al. . |
| 5,276,057 | 1/1994 | Milgram et al. . |
| 5,304,379 | 4/1994 | Cormier et al. . |
| 5,332,576 | 7/1994 | Mantelle ............................ 424/443 |
| 5,354,885 | 10/1994 | Milman et al. . |
| 5,387,615 | 2/1995 | Milgram et al. . |
| 5,444,095 | 8/1995 | Tatton et al. . |
| 5,446,070 | 8/1995 | Mantelle . |
| 5,607,691 | 3/1997 | Hale et al. ........................... 424/449 |

FOREIGN PATENT DOCUMENTS

WO 96/26720  9/1996  WIPO ........................ A61K 31/35

OTHER PUBLICATIONS

Buys, et al., "(-)-Deprenyl Increases the Survival of Rat Retinal Ganglion Cells After Optic Nerve Crush," *Current Eye Res.* 14 :119–126 (1995).

Chrisp, et al., "Selegiline, A Review of Its Pharmacology, Symptomatic Benefits and Protective Potential in Parkinson's Disease," *Drugs & Aging 1* :228–248 (1991).

Feigin, et al., "A Double–Blind, Placebo–Controlled, Cross–Over Study of Deprenyl in Children With Tourette's Syndrome (TS) and Attention–Deficit Hyperactivity Disorder (ADHD)," *Neurology* 45:A254–A255 (1995).

Green, "The Treatment of Attention–Deficit Hyperactivity Disorder With Nonstimulant Medications," *Pediatric Psychopharmacol.* 4:169–195 (1995).

Jankovic, "Deprenyl in Attention Deficit Associated With Tourette's Syndrome," *Arch. Neurol.* 50:286–288 (1993).

Rapoport, et al., "New Drug Trials in Attention Deficit Disorder," *Psychopharmacol. Bull.* 21:232–236 (1985).

Trope, et al., "(-) Deprenyl Improves Visual Function in Glaucoma Patients," *Invest. Ophthalmol. & Vis. Science 35* :2178 (1994).

Zametkin, et al., "Noradrenergic Hypothesis of Attention Deficit Disorder With Hyperactivity: A Critical View," *Psychopharmacology: The Third Generation of Progress*, Herbert Y. Meltzer, Editor, Raven Press, New York, 837–842 (1987).

Heinonen et al, Clinical Pharmacology & Therapeutics, vol. 56, No. 6, pp. 742–49, 1994.

*Primary Examiner*—James H. Reamer
*Attorney, Agent, or Firm*—Michael A. Sanzo; Vinson & Elkins L.L.P.

[57] ABSTRACT

The present invention is directed to improved methods for treating certain selegiline-responsive diseases or conditions and, more specifically, to methods in which selegiline is administered buccally or sublingually. Selegiline may be used ether as a free base or as a pharmaceutically acceptable acid addition salt. The selegiline-responsive diseases or conditions include neuronal-degenerative diseases and conditions, such as Alzheimer's disease and neuronal damage from hypoxia, stroke, ischemia, and trauma, and dopaminergic-related, selegiline responsive diseases and conditions such as depression and ADHD.

20 Claims, No Drawings

SUBLINGUAL AND BUCCAL ADMINISTRATION OF SELEGILINE FOR TREATING CERTAIN SELEGILINE-RESPONSIVE DISEASES AND CONDITIONS

This application is a continuation of PCT/US96/17745 filed Nov. 5, 1995. Provisional Appln. No. 60/007,325 filed Nov. 6, 1995.

FIELD OF THE INVENTION

The present invention pertains to improved methods for using selegiline in therapeutic applications. In particular, the invention is directed to improved methods for treating certain selegiline-responsive diseases and conditions by administering selegiline either buccally or sublingually.

BACKGROUND OF THE INVENTION

Selegiline, including its acid addition salt forms, has heretofore been known to be useful for veterinary and clinical purposes because of its neuronal-protective or neuronal-regenerative effects and is dopaminergic effects, i.e., its selective inhibition of the enzymatic degradation of dopamine by monoamine oxidase B. Selegiline, i.e., R-(-)-N-methyl-N-(prop-2-ynyl)-2-aminophenylpropane, also known as L-(-)-deprenyl or R-(-)-deprenyl, has the following structural formula:

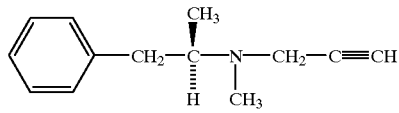

The discovery of selegiline initially represented an important therapeutic improvement over known non-selective monoamine oxidase inhibitors, e.g., tranylcypromine. Tranylcypromine was introduced more than thirty years ago for the treatment of depression, but was subsequently withdrawn from clinical use because of a severe hypertensive side effect, the so-called "cheese effect". Tranylcyproamine was non-selective with respect to the two distinct monoamine oxidase enzymes: monoamine oxidase A (MAO-A) and monoamine oxidase B (MAO-B). In particular, the cDNAs encoding these enzymes show different promoter regions and distinct exon portions, indicating they are encoded independently at different gene positions, and analysis of the two proteins has shown differences in their respective amino acid sequences.

The relative selectivity of selegiline in the inhibition of MAO-B is important to its safety profile following oral administration. The "cheese effect" and resulting acute toxicity of tranylcypromine arises from its inhibition of MAO-A, which interferes with the metabolism of tyramine. Tyramine is normally metabolized in the gastrointestinal tract by MAO-A. However, when MAO-A is inhibited, tyramine absorption is increased following consumption of tyramine-containing foods such as cheese, beer, herring, etc. This results in the release of catecholamines which can precipitate a hypertensive crisis, producing the "cheese effect." This effect is characterized by Goodman and Gilman as the most serious toxic effect associated with MAO-A inhibitors. Although selegiline is a selective inhibitor of MAO-B at certain dosages and conditions, it produces undesirable inhibition of MAO-A when administered under other conditions, e.g., higher doses. Thus, tyramine sensitivity and the risk of hypertensive crisis increases following oral administration to a human of oral doses of selegiline greater than about 10 mg.

More recently, selegiline has been determined to exhibit direct neuronal effects that may be independent of its MAO-B inhibitory activity. Thus, selegiline is known to be useful for treating diseases and condition associated both with the aforedescribed dopaminergic effect and the more recently characterized neuronal protective or regenerative effect.

Because of these significant pharmacological effects, selegiline is known to be useful in a significant variety of diseases and conditions. For example, U.S. Pat. No. 4,861,800 (Buyske) discloses the use of selegiline in the treatment of depression, Alzheimer's disease and Parkinson's disease, particularly through the use of transdermal dosage forms, including ointments, creams and patches. U.S. Pat. No. 5,242,950 (Hastings) discloses the use of selegiline in the treatment of macular degeneration. U.S. Pat. No. 5,151,449 (Milgram) discloses the use of selegiline in the treatment of age-dependent degeneracies, including age-dependent weight loss, the loss of renal function and the loss of cognitive function, including spatial learning ability. U.S. Pat. No. 5,276,057 (Milgram and Stevens) discloses the use of selegiline in the treatment of immune system dysfunction. U.S. Pat. No. 5,151,419 discloses the use of selegiline in the treatment of schizophrenia. PCT Published Application WO 92/17169 and U.S. Pat. No. 5,444,095 disclose the use of selegiline in the treatment of neuromuscular and neurodegenerative disease and in the treatment of CNS injury due to hypoxia, hypoglycemia, ischemic stroke or trauma; neurotoxic agents (e.g. MPTP); or amyotrophic lateral sclerosis. (ALS). Selegiline provides neuroprotection or neuronal rescue, by one or more mechanisms, for example, by reducing oxidative neuronal damage, increasing the amount of the enzyme superoxide dismutase, and/or reducing dopamine catabolism. PCT Published Application WO 92/17169 discloses that selegiline acts by directly maintaining, preventing loss of, and/or assisting in, the nerve function of animals.

In addition, selegiline has been disclosed as being useful in the treatment of glaucoma and impotence. See Trope, G. E., et al, "(-)-Deprenyl Improves Visual Function in Glaucoma Patients," Investigative Ophthalmology & Visual Science, 34:2178 (Mar. 15, 1994). See also, Knoll, J., et al, "Long-lasting true aphrodisiac effect of (-)-deprenyl in sluggish old male rats," Mod. Problems Pharmacopsychiatry 19:135–153 (1983) and "Sexually low performing male rats die earlier than their high performing peers and selegiline eliminates this difference," Life Sciences 54:1047–1957 (1994).

U.S. Pat. No. 5,192,808 (Ruehl) discloses the use of selegiline in the treatment of pituitary-dependent Cushing's disease. For example, in Cushing's disease, the selegiline-like therapeutic effects may be observed in any of a number of common tests used in diagnosing and monitoring the disease (for a discussion of specific tests see, U.S. Pat. No. 5,192,808).

Selegiline has also been demonstrated to have clinical efficacy in the treatment attention-deficit, hyperactivity disease (ADHD) and Tourette's Syndrome (TS). See Feigin, A., "A Double-Blind, Placebo-Controlled, Cross-over study of Deprenyl in Children with Tourette's Syndrome (TS) and attention-Deficit Hyperactivity Disorder (ADHD)," Neurology 45 (Suppl. 4):337P (April 1995).

Selegiline is known to be useful when administered to a subject through a wide variety of routes of administration and dosage forms. For example U.S. Pat. No. 4,812,481

(Degussa AG) discloses the use of concomitant selegiline-amantadine therapy in which selegiline is used with amantadine in oral, peroral, enteral, pulmonary, rectal, nasal, vaginal, lingual, intravenous, intraarterial, intracardial, intramuscular, intraperitoneal, intracutaneous, and subcutaneous formulations.

Buccal and sublingual compositions of selegiline have been described. U.S. Pat. No. 5,192,550 (Alza Corporation) describes a dosage form into which selegiline may be incorporated comprising an outer wall with one or more pores in which the wall is impermeable to deprenyl, but permeable to external fluids. This dosage form is disclosed to be applicable for oral, sublingual or buccal administration. Similarly, U.S. Pat. No. 5,387,615 discloses a variety of selegiline compositions, including tablets, pills, capsules, powders, aerosols, suppositories, skin patches, parenterals, and oral liquids, including oil-aqueous suspensions, solutions, and emulsions. Further disclosed therein are selegiline-containing sustained release (long acting) formulations and devices.

Selegiline is metabolized in vivo in humans into three main metabolites: desmethylselegiline, amphetamine and methamphetamine. One of the metabolites, desmethylselegiline, does in fact inhibit monoamine oxidase B. However, compared to selegiline, inhibitory activity is exceedingly weak. For example, experiments performed in vitro using human platelets have indicated that desmethylselegiline is 68 times less potent than selegiline in inhibiting MAO-B. Similarly, results obtained from mitochondrial-rich fractions from rat cortex and rat brain have indicated that selegiline is approximately 50 times more potent than its desmethyl metabolite as an MAO-B inhibitor and is approximately equal in terms of specificity for MAO-B relative to MAO-A.

The potency of desmethylselegiline as an MAO-B inhibitor in vivo has been reported by Heinonen, E. H., et al., ("Desmethylselegiline, a metabolite of selegiline, is an irreversible inhibitor of MAO-B in human subjects," referenced in Academic Dissertation "Selegiline in the Treatment of Parkinson's Disease," from Research Reports from the Department of Neurology, University of Turku, Turku, Finland, No. 33 (1995), pp. 59–61). According to Heinonen, desmethylselegiline appears to have only one-fifth of the MAO-B inhibitory effect of selegiline in vivo, i.e., a dose of 10 mg of desmethylselegiline would be required to have the same MAO-B effect as 1.8 mg of selegiline.

The two other principal metabolites of selegiline, amphetamine and methampbetamine, are both known to have neurotoxic effects and are therapeutically undesirable (see e.g., Ryan et al., "Histological and ultrastructural evidence that D-amphetamine causes degeneration in neostriatum and frontal cortex of rats," *Brain Res.* 518:76–77 (1990); Pu et al., "The effects of amfonelic acid, a dopamine uptake inhibitor, on methamphetamine-induced dopaminergic terminal degeneration and astrocytic response in rat striatum," *Brain Res.* 649:217–224 (1994); Ellison, "Continuous amphetamine and cocaine have similar neurotoxic effects in lateral habenular nucleus and fasciculus retroflexus," *Brain Res.* 598:353–356 (1992)).

The present invention is based upon the discovery that certain diseases and conditions for which selegiline is known to be useful are surprisingly and unexpectedly more advantageously treated by administering selegiline buccally or sublingually rather than by administering selegiline using prior art methods, e.g., oral administration. Accordingly, the novel methods disclosed herein produce enhanced therapeutic effects.

SUMMARY OF THE INVENTION

The present invention particularly includes:

an improved method for obtaining a selegiline-like therapeutic effect in a mammal suffering from (a) a neuronal-degenerative, selegiline-responsive disease or condition, (b) depression, or (c) attention-deficit, hyperactivity disease (ADHD), comprising:

administering selegiline, or a pharmaceutically acceptable salt thereof, to said mammal in a buccal or sublingual dosage form, wherein said selegiline, or pharmaceutically acceptable salt thereof, is administered in an amount sufficient to produce a selegiline-like therapeutic effect.

The present method is employed in any neuronal-degenerative condition or disease in which selegiline produces a beneficial therapeutic effect. For the purposes of the present invention, the term "neuronal-degenerative" refers to those diseases or conditions where the effect of selegiline is not associated with any known dopaminergic effects. Thus, for example, the term excludes reference to diseases like Parkinson's Disease, depression, and attention-deficit, hyperactivity disease in which dopaminergic activity is reported to be implicated in the therapeutic action of selegiline.

However, the term "neuronal-degenerative" does refer to selegiline-responsive diseases and conditions leading to, or caused by, neuronal degeneration in which selegiline has a favorable effect on the survival of the neurons implicated in the disease condition. Included among these are those directly associated with neuronal damage, for example, injury due to hypoxia, ischemia, stroke; trauma (e.g., damage due to mechanical injury), and chemotoxic damage. Moreover, neuronal-degenerative diseases and conditions encompass those conditions in which neuronal dysfunction or death is part of a more complex etiologic process, for example, Alzheimer's disease and other neurodegenerative dementias, multiple sclerosis, and amyotrophic lateral sclerosis (ALS). In either event, the typical selegiline-like therapeutic effects would include a reduction in the number of neurons damaged or lost; increased neuronal regrowth; improved cognitive and physical capabilities; and improved memory (see U.S. Pat. No. 5,444,095; U.S. Pat. No. 5,225,446; and PCT application WO 92/17169).

Finally, the neuronal degenerative processes included within the ambit of the present method include those where neuronal loss is attributable to the aging process or other pathologies. Among these neuronal-degenerative conditions are weight loss; diabetic and related neuropathies, loss of renal function and immune system dysfunction. Typical selegiline-like therapeutic effects would include reduced weight loss; reduced blood urea nitrogen levels; reduction in the age related proliferation of peripheral blood lymphocytes; maintenance of a higher CD4/CD8 ratio; and increased blood levels of antigen-specific immunoglobulins after antigen challenge (see U.S. Pat. Nos. 5,151,449;.5,276, 057 and 5,387,615).

Glaucoma and macular degeneration represent two visual conditions that have been reported as being amenable to selegiline treatment in accordance with the present method. In particular, selegiline is thought to improve the visual acuity of animals with these conditions. The present method, in which selegiline is delivered buccally or sublingually, represents an improvement in this treatment (see U.S. Pat. No. 5,242,950).

The present method may also be applied to certain selegiline-responsive diseases and conditions where the dopaminergic activity of selegiline is known to produce a useful therapeutic response. These selegiline-response diseases are referred to herein as "dopaminergic-related, selegiline-responsive diseases or conditions." The dopaminergic-related, selegiline responsive diseases or conditions of the present invention are: attention-deficit, hyperactivity disease (ADHD) and Tourette's syndrome, depression, post-polio syndrome, narcolepsy, chronic fatigue syndrome, schizophrenia, tardive dyskinesia, alopecia, and the treatment of pituitary-dependent Cushing's disease.

The total daily dosage of selegiline administered to an animal or patient, typically a human patient, should be at least the amount required to induce a selegiline-like therapeutic effect. The term "selegiline-like therapeutic effect" refers to one of the known therapeutic or prophylactic effects of selegiline in an animal or patient. Typical therapeutic effects would include: an increase in neuronal survival after trauma or in response to a neurodegenerative disease; reduced loss of cognitive or physical capabilities; reduced loss of memory; retardation of age dependent weight loss or immune system dysfunction; improved renal function; and reduced loss of vision.

The actual dosage required to effect such a result is influenced by a number of clinical factors, but will preferably require at least about 0.0015 mg per kg of body weight of selegiline per day and, more preferably, between about 0.01 and 0.15 mg/kg per day. Dosage is calculated on the basis of the free secondary amine form of selegiline and may be provided in either a single or multiple dosage regimen. The optimal daily dose of selegiline useful for the purposes of the present invention is determined by methods known in the art and will be influenced by factors such as the condition or disease being treated, the severity of the condition or disease, the condition of the subject to whom treatment is being given, the desired degree of therapeutic response, and the concomitant therapies being administered to the patient or animal. Ordinarily, the attending physician or veterinarian will administer an initial daily dose of at least about 0.01 mg per kg of body weight, calculated on the basis of the free secondary amine, with progressively higher doses being employed depending upon the response to the therapy. Typically, the daily dose will be about 0.01 mg/kg of body weight and may extend to about 0.15 mg/kg of body weight (all such doses again being calculated on the basis of the free secondary amine). These are simply guidelines since the actual dose must be carefully selected and titrated by the attending physician or veterinarian depending upon the age, weight, clinical condition and observed response of the individual patient or animal.

The daily dose can be administered in a single or multiple dosage regimen.

Buccal and sublingual dosage forms of selegiline are prepared utilizing known techniques, e.g., the techniques described for example in U.S. Pat. No. 5,192,550; U.S. Pat. No. 5,221,536; U.S. Pat. No. 5,266,332; U.S. Pat. No. 5,057,321; U.S. Pat. No. 5,446,070; U.S. Pat. No. 4,826,875; U.S. Pat. No. 5,304,379; or U.S. Pat. No. 5,354,885.

Buccal or sublingual formulations for use in the present methods may employ selegiline either in the form of a free base or as a pharmaceutically acceptable acid addition salt. In the latter case, the hydrochloride salt is generally preferred. However, other salts useful in the present invention include those derived from organic and inorganic acids such as, without limitation, hydrobromic acid, phosphoric acid, sulfuric acid, methanesulphonic acid, acetic acid, tartaric acid, lactic acid, succinic acid, citric acid, malic acid, maleic acid, aconitic acid, salicylic acid, phthalic acid, embonic acid, enanthic acid, and the like.

The methods disclosed herein may be used for both human and non-human subjects. With regard to the latter, the methods are particularly, but not exclusively, directed to domes-ticated mammals such as canine and feline species.

DETAILED DESCRIPTION OF THE INVENTION

EXAMPLE 1

Buccal Selegiline Tablet

A buccal tablet is formulated from the following ingredients:

| Ingredient | Weight (mg/unit dose) |
| --- | --- |
| Selegiline HCl | 5.00 |
| Hydroxypropylmethlycellulose (HPMC) | 5.00 |
| Lactose | 186.00 |
| Citric Acid (anhydrous) | 2.00 |
| Magnesium stearate | 2.00 |

Prepare a granulate from the first four ingredients by first passing ingredients 1, 3 and 4 though a 25-mesh hand screen and thereafter blend. Prepare a 10% solution of HPMC in water (10 g HPMC per 100 g of solution) and granulate this solution into the dry ingredients. Pass the wet mass through a #10 screen and spread onto a paper-lined tray, drying for three hours at 130° C. Blend the resulting granulate with ingredient 5 and compress into a tablets.

EXAMPLE 2

Sublingual Selegiline Tablet (Non-Effervescent)

A sublingual tablet is prepared from the following ingredients:

| Ingredient | Weight (mg/unit dose) |
| --- | --- |
| Selegiline HCl | 5.00 |
| Croacarmellose sodium | 5.00 |
| Lactose | 186.00 |
| Citric Acid (anhydrous) | 2.00 |
| Magnesium stearate | 2.00 |

Pass the first three ingredients above through a 25-mesh hand screen and blend and mix for seven minutes. After passing ingredient 4 above through a #60 hand mesh, add to the mix with the remaining blended ingredients and blend for an additional 3 minutes. Compress the resulting mixture into tablets.

EXAMPLE 3

Sublingual Selegiline Tablet (Effervescent)

A sublingual tablet is prepared from the following ingredients:

| Ingredient | Weight (mg/unit dose) |
| --- | --- |
| Selegiline HCl | 5.00 |
| Citric Acid (anhydrous) | 100.00 |
| Sodium bicarbonate | 185.00 |
| Fumaric acid | 10.00 |

The compositions, prepared above, or known buccal or sublingual compositions, or buccal or sublingual compositions prepared using known methods are then employed in the methods described above.

I claim:

1. An improved method for obtaining a selegiline-like therapeutic effect in a mammal suffering from (a) a neuronal-degenerative, selegiline-responsive disease or condition, (b) depression, or (c) attention-deficit, hyperactivity disease (ADHD), comprising:

administering selegiline, or a pharmaceutically acceptable salt thereof, to said mammal in a buccal or sublingual dosage form, wherein said selegiline, or pharmaceutically acceptable salt thereof, is administered in an amount sufficient to produce a selegiline-like therapeutic effect.

2. A method of claim 1, wherein selegiline is administered as the free base.

3. A method of claim 1, wherein said selegiline is administered as a pharmaceutically acceptable acid addition salt.

4. A method of claim 3, wherein said pharmaceutically acceptable acid addition salt is the hydrochloride salt.

5. A method of claim 4, wherein said mammal is a human.

6. A method of claim 5, wherein said disease or condition is a consequence of hypoxia, ischemia, or stroke.

7. A method of claim 5, wherein said neuronal degeneration is due to trauma.

8. A method of claim 5, wherein said disease or condition is Alzheimer's disease.

9. A method of claim 5, wherein said disease or condition is ALS.

10. A method of claim 5, wherein said disease or condition is age dependent weight loss.

11. A method of claim 5, wherein said disease or condition is characterized by immune system dysfunction.

12. A method of claim 5, wherein said disease or condition is Cushing's disease.

13. A method of claim 5, wherein said disease or condition is glaucoma.

14. A method of claim 5, wherein said disease or condition is macular degeneration.

15. A method of claim 5, wherein said disease or condition is attention deficit, hyperactivity disease (ADHD).

16. A method of claim 5, wherein said disease or condition is depression.

17. A method of claim 5, wherein said disease or condition is a loss of renal function.

18. A method according to any of the preceding claims wherein the dose of selegiline is greater than about 0.01 mg/kg/day.

19. A method according to any of the preceding claims wherein the administration is buccal.

20. A method according to any of the preceding claims wherein the administration is sublingual.

* * * * *

UNITED STATES PATENT AND TRADEMARK OFFICE
CERTIFICATE OF CORRECTION

PATENT NO. : 6,117,912
DATED : September 12, 2000
INVENTOR(S) : Anthony R. DiSanto It is certified that error appears in the above-identified patent and that said Letters Patent are hereby corrected as shown below:

In claims 2-20, columns 7, lines 26-32 and column 8, lines 1-31, delete the initial word "A" and insert --The-- therefor.

Signed and Sealed this

Twenty-fourth Day of April, 2001

Attest:

NICHOLAS P. GODICI

Attesting Officer
Acting Director of the United States Patent and Trademark Office